(12) United States Patent
Brandenburger

(10) Patent No.: US 12,734,309 B2
(45) Date of Patent: Sep. 15, 2026

(54) SYRINGE, SYRINGE BODY AND METHOD FOR THE PRODUCTION THEREOF

(71) Applicant: Fresenius Kabi Deutschland GmbH, Bad Homburg (DE)

(72) Inventor: Torsten Brandenburger, Reichelsheim (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 924 days.

(21) Appl. No.: 17/759,513

(22) PCT Filed: Apr. 22, 2021

(86) PCT No.: PCT/EP2021/060469
§ 371 (c)(1),
(2) Date: Jul. 26, 2022

(87) PCT Pub. No.: WO2021/214193
PCT Pub. Date: Oct. 28, 2021

(65) Prior Publication Data

US 2023/0040207 A1 Feb. 9, 2023

(30) Foreign Application Priority Data

Apr. 24, 2020 (EP) .................................... 20171399

(51) Int. Cl.
*A61M 5/34* (2006.01)
*A61M 5/00* (2006.01)
*A61M 5/31* (2006.01)

(52) U.S. Cl.
CPC ............ *A61M 5/347* (2013.01); *A61M 5/002* (2013.01); *A61M 5/3129* (2013.01);
(Continued)

(58) Field of Classification Search
CPC ..... A61M 5/347; A61M 5/3134; A61M 5/345
See application file for complete search history.

(56) References Cited

U.S. PATENT DOCUMENTS 5,782,815 A 7/1998 Yanai et al.
6,331,174 B1 12/2001 Reinhard et al.
(Continued)

FOREIGN PATENT DOCUMENTS

CN 104780960 A 7/2015
CN 109562226 A 4/2019
(Continued)

OTHER PUBLICATIONS

International Search Report with English translation and Written Opinion, counterpart International Appl. No. PCT/EP2021/060469 (May 10, 2021) (11 pages).

(Continued)

*Primary Examiner* — Emily L Schmidt
(74) *Attorney, Agent, or Firm* — Cook Alex Ltd.

(57) ABSTRACT

The disclosure relates to a syringe, comprising a syringe body with a nozzle and a threaded connection. The syringe body comprises a side wall and a front wall, wherein the syringe body comprises a cycloolefin as a first material, at least in portions. The first material forms an internal wall of the syringe body. The threaded connection comprises, at least in portions, as a second material a material other than the cycloolefin, wherein the first and the second material are integrally bonded to one another. The second material extends in the region of the front wall at least in portions over the first material, so that the front wall comprises, at least in portions, a two-layer region. The first and the second material in the two-layer region have a mutually engaging structure.

20 Claims, 8 Drawing Sheets

(52) U.S. Cl.
CPC .......... *A61M 5/3134* (2013.01); *A61M 5/345* (2013.01); *A61M 2205/0238* (2013.01); *A61M 2207/10* (2013.01)

(56) References Cited

U.S. PATENT DOCUMENTS

| | | | | |
|---|---|---|---|---|
| 2011/0139830 | A1 | 6/2011 | Hasegawa et al. | |
| 2015/0246185 | A1 | 9/2015 | Heinz | |
| 2016/0175532 | A1* | 6/2016 | Gutierrez ............ | A61M 5/3137<br>604/218 |
| 2016/0331902 | A1 | 11/2016 | Carlyon | |
| 2018/0043102 | A1 | 2/2018 | Cojocariu et al. | |
| 2018/0050158 | A1* | 2/2018 | Baldauf ............... | B65D 75/366 |
| 2018/0207324 | A1 | 7/2018 | Auerbach et al. | |
| 2020/0101238 | A1 | 4/2020 | Auerbach et al. | |
| 2020/0114084 | A1 | 4/2020 | Kücük | |

FOREIGN PATENT DOCUMENTS

| | | |
|---|---|---|
| DE | 102017112823 | 12/2018 |
| EP | 3342441 | 7/2018 |
| EP | 3636302 | 4/2020 |
| WO | WO2012/101669 | 8/2012 |

OTHER PUBLICATIONS

Chinese Office Action and Search Report (with English-language translation), counterpart Chinese Patent App. No. 202180030660.2 (Jun. 9, 2025) (18 pages).

* cited by examiner

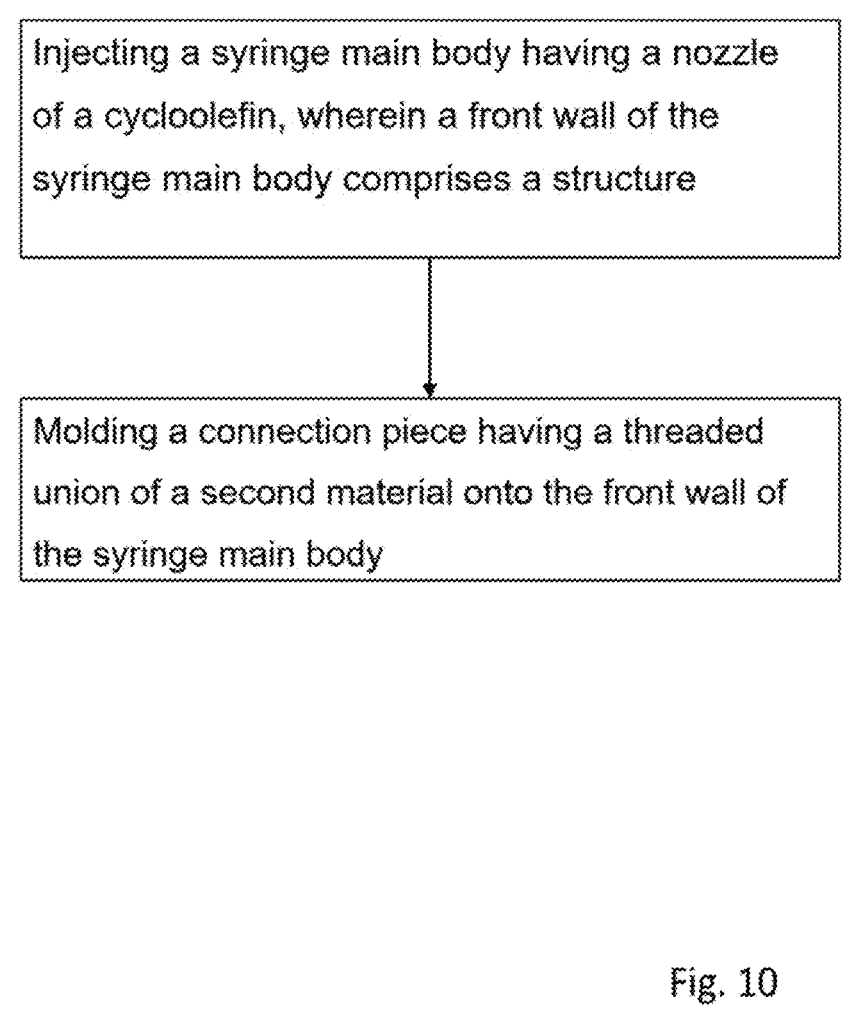

Injecting a syringe main body having a nozzle of a cycloolefin, wherein a front wall of the syringe main body comprises a structure Molding a connection piece having a threaded union of a second material onto the front wall of the syringe main body

Fig. 10

SYRINGE, SYRINGE BODY AND METHOD FOR THE PRODUCTION THEREOF

The present application is a U.S. National Stage of PCT International Patent Application No. PCT/EP2021/060469, filed Apr. 22, 2021, which claims priority to EP Application Serial No. 20171399, filed Apr. 24, 2020, both of which are hereby incorporated herein by reference.

FIELD OF THE INVENTION

The invention relates to a syringe pre-filled with a medical fluid, comprising a syringe body having a Luer lock connection and to a method for manufacturing the syringe body.

BACKGROUND OF THE INVENTION

Pre-filled syringes, which are also designated as single-use syringes, can comprise a syringe body of plastic. In order to deliver the medical fluid contained therein, the syringe body has a nozzle on its end face. The nozzle serves for example to connect a needle or a hose of a transfer system. Syringes with a male Luer lock connection are in particular widely used. In this case, the nozzle, which is formed conically as standard, is surrounded by a sleeve with an internal thread.

In particular in the case of pre-filled syringes, a suitable plastic material should meet different requirements.

The plastic material should be suitable for as many different medical fluids as possible. In particular a diffusion of components of the medical fluid into the material and also leakage of material components through the medical fluid should largely be avoided, even when stored for a long time. Additionally, a suitable plastic material should also be autoclavable.

Cycloolefin copolymers have become established as particularly suitable materials. On the one hand, they are easy to process in an injection-molding process. On the other hand, they are characterized by high stiffness and high hardness whilst also being relatively lower density. Furthermore, such materials are amorphous and highly-transparent. They also have a low water absorption and a low water vapor permeability.

These plastics can, however, be relatively brittle. For example, compared with polypropylene or polyethylene, cycloolefin copolymers have a relatively low elongation at break. This can for example lead to the Luer lock thread of the syringe becoming damaged when the connection of a transfer system is tightened incorrectly. Due to the brittleness of the material, the material cannot deform considerably plastically such that damage of this type can take place quite abruptly. Thus, the user has almost no tactile feedback that they are tightening the connection too much.

To reduce this problem, the published patent application DE 10 2017 112 823 A1 provides a strengthened portion of the threaded sleeve using ribs. The mechanical stability of the threaded connection is improved in this way.

The published patent application EP 3 342 441 A1 proposes to provide the threaded connection of a different material compared to the syringe body. It is in particular provided that the connection piece of softer material is molded onto the rest of the syringe main body.

OBJECT OF THE INVENTION

Therefore, the object underlying the invention is to at least reduce the mentioned problems of the state of the art.

It is in particular an object of the invention to provide a syringe of plastic pre-filled with a medical fluid, which comprises an internal wall of a material with high chemical resistance and good barrier effect, and which is also provided with a stable threaded connection of plastic.

SUMMARY OF THE INVENTION

The object of the invention is achieved by a syringe body, by a syringe and by a method for manufacturing a syringe body according to the independent claims.

Preferred embodiments and further developments of the invention can be inferred from the subject matter of the dependent claims, the description as well as the drawings.

According to a first aspect, the invention relates to a syringe body for a syringe, comprising a syringe main body having a side wall, a front wall and a nozzle arranged on a front side of the front wall,

- wherein the syringe main body comprises, at least in portions, a cycloolefin as the first material, which forms at least one internal wall of the syringe main body,
- wherein a connection piece with a threaded connection is arranged with its rear side on the front side of the front wall of the syringe main body and the connection piece, in particular at least in portions, comprises as a second material, a material other than the first material,
- wherein the syringe main body and the connection piece are integrally bonded to one another to form the syringe body
- and wherein a structure on the front side of the front wall of the syringe main body and a complementary structure on the rear side of the connection piece engage into one another.

The invention in particular provides that at least the internal wall, preferably the entire side wall, of the syringe main body comprises a cycloolefin. In particular, the entire syringe main body is provided by a cycloolefin.

The first material preferably consists of at least 50% by weight, particularly preferably at least 90% by weight, of a cycloolefin.

A cycloolefin within the meaning of the invention is understood as all cycloolefin copolymers, which are obtained by catalyzed copolymerization of cycloolefins. Within the meaning of the invention, cycloolefins are also understood as materials, which are obtained by a ring-opening salt metathesis. These are, strictly speaking, not designated as cycloolefin copolymers, but as cycloolefin polymers. The cycloolefin can also be formed as a crystal clear polymer.

Such materials are amorphous, transparent and, to a significantly lesser degree than other plastics, interact with the filled medical fluid, in particular with an aqueous medical fluid or an emulsion.

According to the invention, the syringe body is formed of the syringe main body and the connection piece, wherein the connection piece comprising the threaded connection is formed of a different material to the syringe main body.

In order to achieve a good integrally bonded connection, in particular through manufacture in an injection-molding process, the connection piece with the threaded connection is formed in such manner that the second material, at least on the end face, covers the first material at least in portions. As a result, at least the end surface of the syringe body is formed in two layers at least in portions.

In the region of the two-layer front wall, the first and the second material comprise a mutually engaging structure.

A structure is understood as a regular or irregular vertical profile of the first material with protrusions or depressions. The second material, which is molded on e.g. in the injection-molding process, engages into the depressions. The structure can also be viewed as a profile with peaks and troughs, wherein the troughs are filled by the respectively other material. The surfaces adjoining one another at a boundary area inside the two-layer region made of the first and the second material each comprise a surface relief with a profiled structure which is filled by the respectively other material.

It has been found that the tendency of the two layers to separate in particular during autoclaving and/or during mechanical stresses, can be notably reduced as a result.

Strains, for example due to different thermal expansion coefficients of the materials, are distributed not only substantially radially along a smooth surface, but are partially diverted into the axial direction due to the peaks and troughs.

The linear heat expansion coefficient for cycloolefin copolymers (under standard conditions) is generally below $60\times10^{-6}\times K^{-1}$. In contrast, polypropylenes have for example a notably higher coefficient of thermal longitudinal expansion, in particular of over $150\times10^{-6}\times K^{-1}$.

In spite of the strength and a certain brittleness of the cycloolefin copolymer, the integrally-bonded connection does not break in particular during an autoclaving process due to different thermal expansion of the two materials.

The size of the surface of a boundary area between the first and the second material is also enlarged by the structure. This boundary area is preferably at least 20% larger compared to an unstructured configuration.

Lastly, a form-fitting connection can be provided between the first and the second material by the structure, in particular with respect to a torque between the parts, when a connector is connected to the threaded connection.

An improved mechanical connection can be hereby provided in a very simple manner.

At the same time, overmolding the nozzle with the second material can preferably be dispensed with. As a result, any contact between the medical fluid and the second material can preferably be avoided when used as intended.

The manufacture of such a syringe is also not associated with significantly increased effort. Thus, an injection-molding tool can be used for manufacturing the syringe main body which comprises a negative profile in the form of the profiling of the syringe main body.

According to the invention, the front side of the front wall of the syringe main body and the rear side of the connection piece are integrally bonded to one another.

In the case of one embodiment of the invention, the connection piece is provided as a separate part, which is mounted on the syringe main body. The connection piece is in particular connected by means of adhering and/or welding to the syringe main body.

In the case of a further embodiment of the integrally-bonded connection, the connection piece is molded onto the syringe main body.

The protrusions can be formed as regular and/or irregular protrusions. The depressions can be formed as regular and/or irregular depressions.

In the case of one embodiment of the invention, the protrusions and/or the depressions are formed as concentric rings. In the case of such profiling, the protrusions and the depressions run in particular radially from inside outwards. As a result, there is in particular a uniform deflection of stresses in the axial direction all around.

The protrusions or depressions can in particular have a substantially triangular cross-section. In the case of this embodiment, the profiling is formed as a saw tooth profile. However, other structures, such as for example a wave shape, in particular a sinusoidal shape, mutually engaging nubs, etc., are also possible.

In the case of one embodiment of the invention, elements of the structure of the first material are formed conically. The elements of the structure, e.g. the webs or nubs, taper upwards. This facilitates provision of the structure of the second layer by molding the second material. In particular, the tendency for bubble formation in the region adjoining the structural elements is reduced.

In the case of one embodiment of the invention, the structure comprises on the front side of the front wall of the syringe main body at least one web and/or one groove, which extends from the nozzle, at least in portions, in the direction of the side wall. Thus, a torsion-proof connection is, so to speak, provided. The elements of the structure can also be formed as nubs and/or wedges.

In one embodiment, the structure of the front wall of the syringe main body can have at least one, preferably a plurality of, webs and/or grooves extending radially. The webs or grooves can hereby have any desired cross-section. However, they are preferably formed with a saw tooth profile.

Owing to the radial alignment, web and groove each form a form-fitting connection, which acts as a torsion-proof connection.

In particular, the structure in top view can have a fan-like and/or star-like configuration. For example, the rods of a fan are formed by radially extending webs and the covering is formed between the webs by the profile extending in a ring-shaped manner. The fan extends around the threaded connection and thereby occupies 360° of the end surface.

The structure can have between 3 and 16, preferably between 6 and 10 radially extending webs and/or grooves distributed around the circumference.

The form-fitting connection provided by the structuring serves in particular to improve the strength of the connection during torque stress, such as for example when tightly screwing in the connection.

In the case of a further development of the invention, a layer of the second material is formed thickened around the threaded connection compared to a radially adjoining region of the layer of the second material. Thus, the material of the second layer is reinforced by a thickened portion, such as for example a bead or an inner bevel, in the transition region from the threaded connection to the front wall. The danger of the threaded connection breaking off when tightened too much is hereby reduced.

In particular, when using a soft second material, the deformation of the material in the region of the front wall is also reduced during tightening, whereby the tendency of the integrally-bonded connection to loosen in this region is in turn reduced.

The second material is preferably a plastic, in particular a transparent plastic, which can be processed in the injection-molding process.

The second material preferably has a higher notch impact toughness than the first material. The second material in particular has a notch impact toughness at least 20%, preferably at least 50%, higher than the first material.

The notch impact toughness is a material characteristic value which defines the tendency of the material to form cracks during dynamic strain. This is determined in the notch bend impact test. The dynamic bending due to the sudden strain causes a break, often without the flow of the material observed during slow strain. In the context of the invention, all material characteristic values, i.e. in particular the notch impact toughness and the following material characteristic values, are determined for standard conditions, i.e. 20° C. and 50% humidity.

The notch impact toughness in the context of the invention is determined according to DIN ISO 179-1 (November 2010). In this case, a test body with a notch standardized in its shape is strained by an impact pendulum. The impact pendulum notches the test body or penetrates it with a defined kinetic energy. Then, the notch is measured or, in the case of penetration, the height at which the pendulum swings back is recorded. From the weight of the impact pendulum and the difference of the pendulum start and end position, the impact energy used can be calculated, with the impact energy representing the product of sample cross-section and notch impact toughness.

Cycloolefins generally have a notch impact toughness of under 3 $kJ/m^2$. In contrast, the second material should have a higher notch impact toughness, in particular of over 3.5 $kJ/m^2$, preferably of over 5 $kJ/m^2$.

A polypropylene can in particular be used as the second material. In particular, partially-crystallized polypropylene has good mechanical properties and is also transparent.

The second material can in particular be softer than the first material. In particular, the second material can have a Shore hardness D (according to DIN ISO 7619-1 (February 2012) of below 75, in particular of below 70. The cycloolefin, in contrast, has a Shore hardness D of over 80 in one embodiment of the invention.

In the case of one embodiment of the invention, the second material has a lower elasticity modulus than the first material. In particular, the elasticity modulus of the second material (according to DIN ISO 527-1 (February 2019) is between 1000 and 1800 MPa. The elasticity modulus of the cycloolefin can in particular be between 1800 and 2200 MPa.

The elongation at break is in particular also an important parameter for the second material. According to one embodiment of the invention, the second material has an elongation at break at least 1.5 times, preferably at least 5 times and particularly preferably at least 10 times, higher than the first material. The elongation at break is also determined according to DIN ISO 527-1. It is indicated as a %.

The cycloolefins used can e.g. have an elongation at break of below 5%, whereas for example a polypropylene used can have an elongation at break of 100% or more.

In order to break the threaded connection, the material must be deformed beyond the upper yield limit. The subsequent deformation in the plastic region of a material with high elongation at break is generally noticed by a trained user such that they recognize that the load-bearing limit of the connection is now actually already exceeded.

In one embodiment of the invention, the structure on the front side of the front wall of the syringe main body is in particular delimited by a radially circumferential web. The structure ends inside the front wall of the syringe main body. The web can in particular be formed by a front section of the side wall of the syringe main body. The highly-transparent impression of the side wall is retained in full as a result.

It is in particular thus provided that the structure ends when the side internal wall is reached. In the case of this embodiment, the side wall thus reaches up to a front edge of the syringe body and the structure ends directly at the side wall. Thus, on the one hand, the entire front wall can be used to provide the structure. On the other hand, the material transition in top view is virtually invisible since it is located precisely on the inner edge of the side wall.

According to one embodiment, the structure of the first and/or of the second material has a maximum structure depth of over 0.1 mm, preferably of over 0.25 mm, and/or of less than 1 mm, preferably less than 0.5 mm. The maximum structure depth is understood as the vertical difference between the tip of a protrusion and the bottom of a depression. The structure is thus a structure in the macro level order of magnitude, whereby force deflection described above is effectively achieved.

The distance from protrusion to protrusion or depression to depression, the so-called structure width, is, in one embodiment of the invention, more than 0.2 mm, preferably more than 0.5 mm, and/or less than 3 mm, preferably less than 1.5 mm.

According to one embodiment of the invention, the ratio of maximum structure depth to structure width can also be more than 0.1, preferably more than 0.25 and/or below 1, preferably below 0.5.

The wall thickness of the layer of the first material is, in the region of the front wall in one embodiment of the invention, 0.3 to 3 times, preferably 0.5 to 1.5 times, the wall thickness of the layer of the second material. The total wall thickness, in particular in the region of the front wall formed in a two-layered manner at least in portions, can e.g. be between 0.3 mm and 5 mm, preferably between 0.6 mm and 2.5 mm.

A syringe comprising a syringe body according to one of the embodiments described above is within the field of the invention, with the syringe having a stopper with which the nozzle is sealed, a plunger and also in particular a plunger rod for delivering the medical fluid via the nozzle. The plunger rod can already be pre-mounted on the plunger or be provided separately.

The syringe according to the invention is preferably filled with a medical fluid, in particular with a fluid containing a medication. The syringe is a pre-filled syringe in this case.

In particular, the syringe is located in a preferably oxygen-impermeable outer packaging, for example a tear-open foil packaging. The syringe, preferably the packaged syringe, is in particular autoclaved. The syringe has been autoclaved in this outer packaging, for example at a temperature of over 110° C., preferably over 120° C. and is thus completely sterile.

According to one embodiment, the medical fluid is an oxygen-sensitive medicinal fluid, for example a medicinal emulsion. According to one embodiment, the medicinal fluid is or comprises propofol, in particular a propofol emulsion. Propofol is described by the chemical name 2,6-Diisopropylphenol (IUAPC).

According to a further aspect, the invention can relate to a syringe, comprising a syringe body having a nozzle and a threaded connection, wherein the syringe body comprises a side wall and a front wall, wherein the syringe body comprises, at least in portions, a cycloolefin, in particular a cycloolefin copolymer or a cycloolefin polymer, as the first material, which forms an internal wall of the syringe body, and wherein the threaded connection comprises, at least in portions, as a second material, a material other than the cycloolefin, wherein the first and the second material are integrally bonded to one another and wherein the second material extends in the region of the front wall, at least in portions, over the first material such that the front wall is formed, at least in portions, in a two-layered manner, wherein the nozzle is formed of the first material and is formed, at least in portions, in a single-layered manner.

The syringe can in particular have any features described above in any desired combination. The two-layer region of the front wall can in particular be formed by a syringe main body with a structure, wherein a mutually engaging structure is provided by a complementary structure of a connection piece. Since the nozzle is not covered, at least in portions, by the second material, any contact of the second material with the medical fluid during intended use is prevented. It has been found that a sufficient mechanical connection between first and second material can still be achieved in particular by an injection-molding process. This can in particular be ensured by the structure described above.

The invention further relates to a method for manufacturing a syringe body.

The method comprises the following steps:

Injecting a syringe main body of a cycloolefin as the first material, wherein a structure with depressions is formed in a front wall of the syringe main body, Molding a connection piece having a threaded connection of a second material onto the front wall of the syringe main body, wherein the depressions of the structure are filled with the second material such that the structure on the front side of the front wall of the syringe main body and a complementary structure formed on the rear side of the connection piece engage into one another.

In this case, an injection-molding tool is used, which comprises the negative of a structure of the front wall of the syringe main body such that a syringe main body with a structured front wall is created.

Then, a connection piece with the threaded connection of the second material is molded onto the front wall. The connection piece forms a complementary structure in the region of the structured front wall of the syringe main body, which, as mentioned above, significantly improves the mechanical connection of both materials.

BRIEF DESCRIPTION OF THE DRAWINGS

The subject matter of the invention will be explained in more detail below on the basis of FIG. 1 to FIG. 10 with reference to exemplary embodiments.

FIG. 10 is a flow diagram of the method steps according to an exemplary embodiment of the method according to the invention.

DETAILED DESCRIPTION OF THE DRAWINGS

Figure 1:
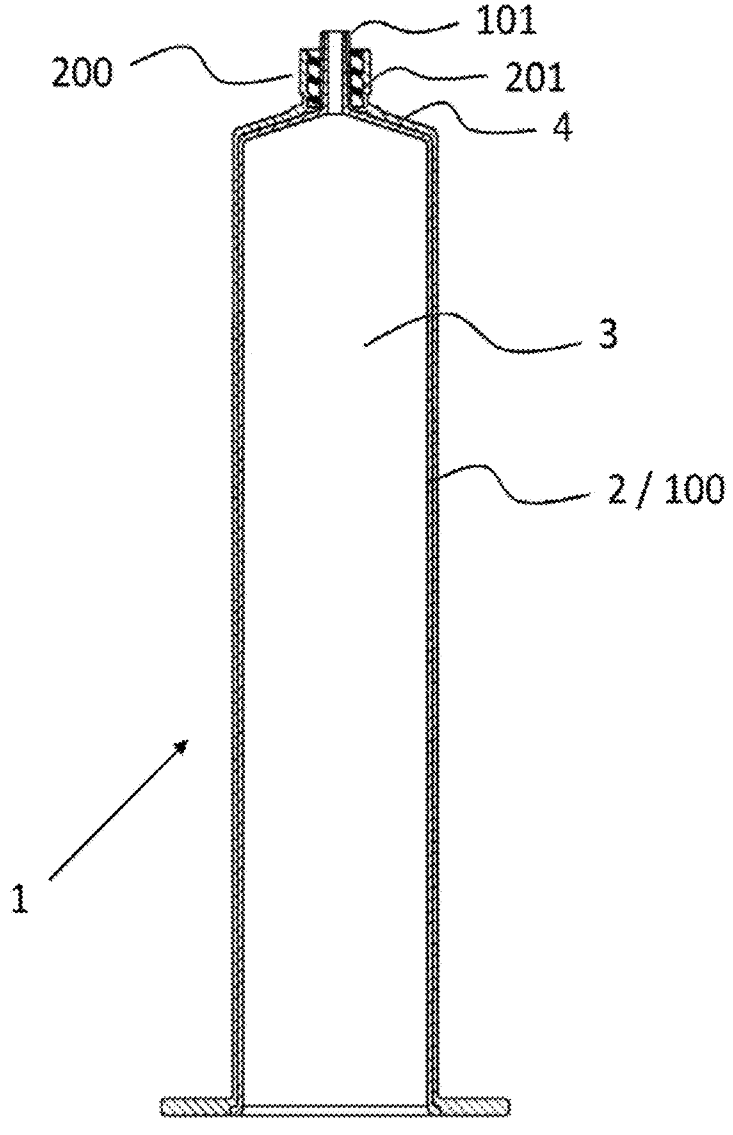
FIG. 1 is an axial sectioned view of a syringe according to a first exemplary embodiment of the invention.

FIG. 1 shows in an axial sectioned view an exemplary embodiment of a syringe 1 according to the invention, wherein in this view only the syringe body 2, but not plunger and plunger rod are represented.

The invention is intended for syringes with virtually any desired volume, in particular of 1 ml to 100 ml.

In the exemplary embodiment according to FIG. 1, a relatively large syringe 1 is represented in particular with an inner volume 3 of roughly 50 ml.

The syringe 1 comprises a nozzle 101 which is preferably formed conically. A threaded connection 201 having an internal thread extends around the nozzle 101. This concerns in particular a male Luer lock connection.

Figure 3:
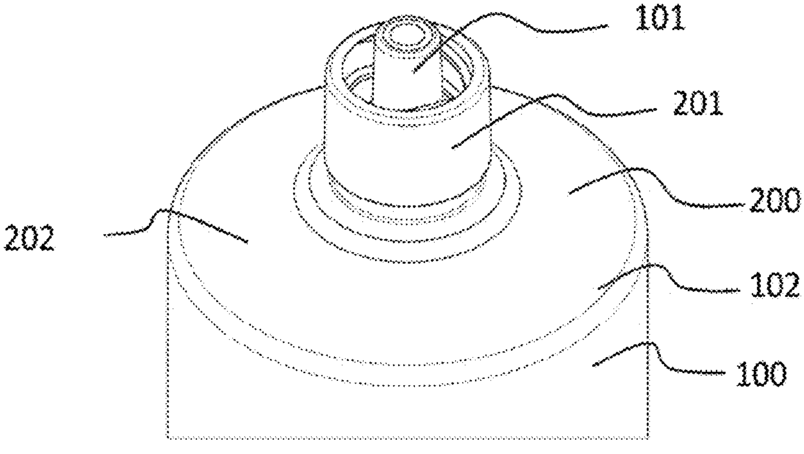
FIG. 3 is a perspective view of the head piece of the syringe or of the syringe body.
Figure 4:
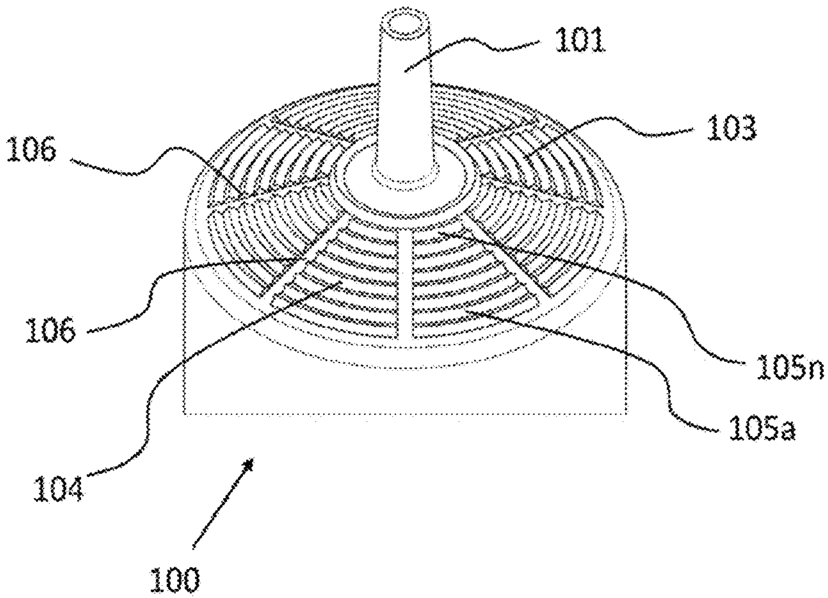
FIG. 4 is a perspective view of the head piece of the syringe main body or of the syringe body without attached connection piece.

It can already be discerned in this sectioned view that in the region of the front wall 4 of the syringe body 2, a two-layer structure of two materials is present (see also FIGS. 3 and 4). In the exemplary embodiment shown, the side wall of the syringe main body is also formed in a two-layered manner and is covered with the second material.

The syringe body 2 comprises a syringe main body 100, which comprises the nozzle 101 and a connection piece 200, which comprises the threaded connection 201.

The side wall 102 of the syringe main body 100 is formed by a first material. The first material is provided by cycloolefin. The second material is also transparent.

Figure 2:
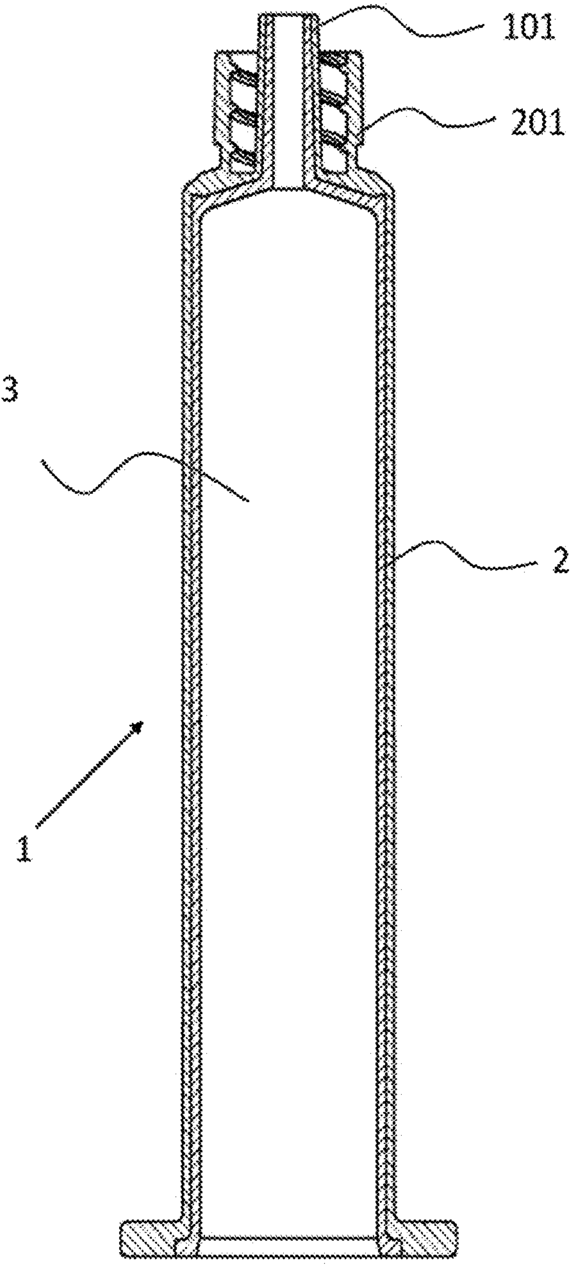
FIG. 2 shows an alternative exemplary embodiment of a syringe.

FIG. 2 is an axial sectioned view of an alternative embodiment of a syringe 1. This exemplary embodiment concerns a relatively small syringe, in particular with an inner volume 3 of roughly 5 ml. The basic structure of the syringe body 2 remains unchanged, however. The dimensions of the connection, consisting of nozzle 101 and threaded connection 201, do not differ from the exemplary embodiment according to FIG. 2. Therefore, the threaded connection 201 has a significantly larger diameter in relation to the maximum diameter of the syringe body 2.

FIG. 3 shows, in a perspective view, the head piece of a syringe 1 according to a further exemplary embodiment of the invention.

The syringe body 2 is formed of the syringe main body 100 and the connection piece 200, which is preferably molded onto the syringe main body 100. The connection piece 200 is formed of a different material to the syringe main body 100. The connection piece 200 is formed by a second material. The mentioned second material is a material other than the first material, for example polypropylene.

The connection piece 200 comprises a front wall 202, which reaches up to the side wall 102 of the syringe main body 100. The threaded connection 201 having an internal thread extends around the nozzle 101, which is part of the syringe main body 100 and which is therefore also formed of the first material, namely of a cycloolefin.

FIG. 4 shows in a corresponding perspective view only the syringe main body 100 of cycloolefin. The front wall 103 of the syringe main body 100 comprises a structure 104, which is preferably provided by the injection molding.

In this exemplary embodiment, the structure 104 of the front wall 103 comprise a plurality of rings **105*a*-105*n* extending concentrically around the nozzle 101**, which are formed here as protrusions.

These rings **105*a*-105*n* are interrupted by a plurality of radially extending grooves 106, which form a torsion-proof connection in cooperation with the molded connection piece 200**.

Figure 5:
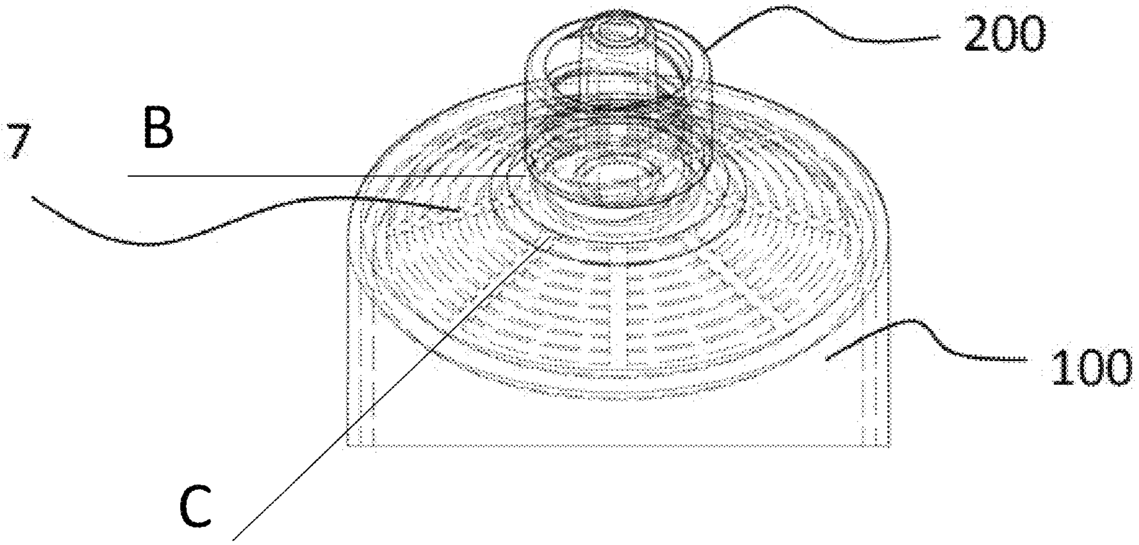
FIG. 5 is a perspective view, wherein the connection piece is represented as a transparent grid.

FIG. 5 is a perspective view, wherein the connection piece 200 is now illustrated as a transparent grid.

In this view, the two-layer region of the front wall of the syringe body 2 is represented, which is formed of the cycloolefin of the syringe main body 100 and a layer of the connection piece 200 of the second material, in particular of polypropylene, arranged on top of it.

The mutually engaging structure is located inside the two-layer region and is formed by the structure 104 of the first material into which the structure 208 of the second material engages.

Figure 6:
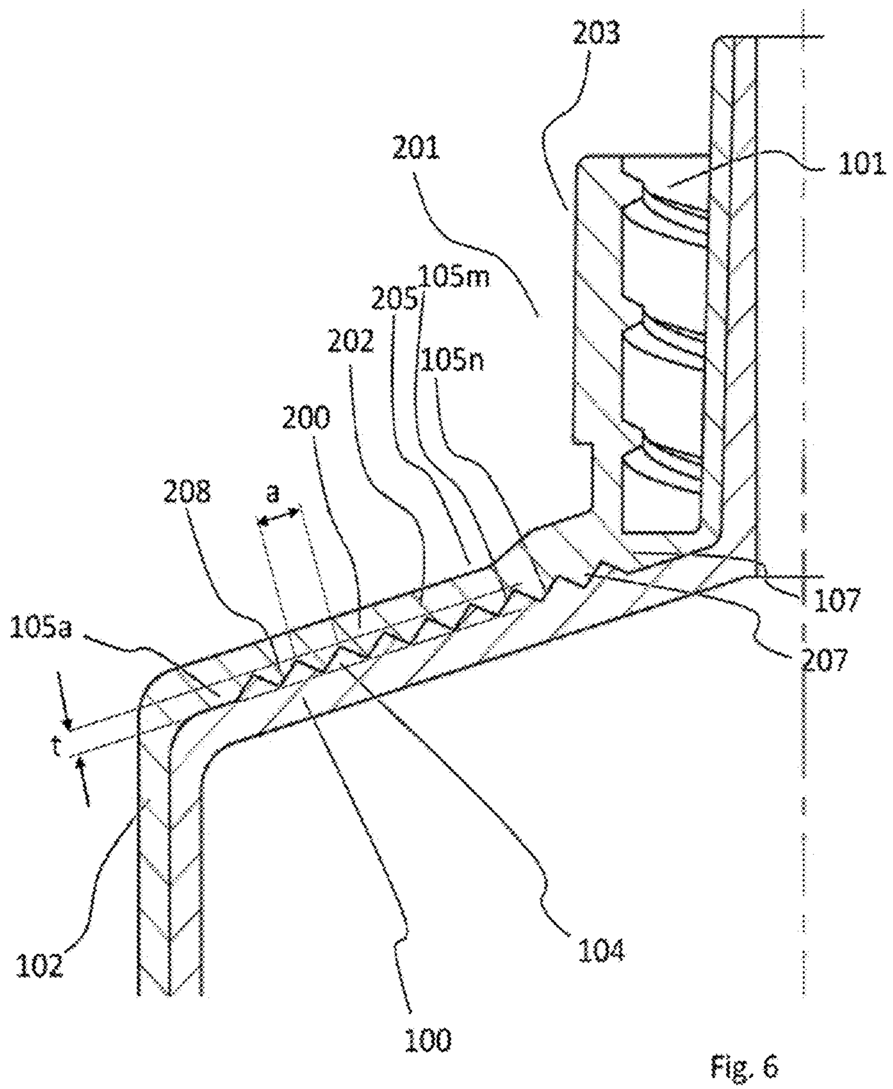
FIG. 6 is a sectioned view along the line B according to FIG. 5.

The mutually engaging structure formed according to the invention is thus, as shown in particular in the detailed representation according to FIG. 6 along the section line B according to FIG. 5, formed by the structure 104 of the syringe main body 100 and by the structure 208 of the connection piece 200 engaging into this structure 104.

The structure 104 of the syringe main body 100 comprises a plurality of teeth 105*a*-105*n* in a radial sectioned view. The structure 104 is formed in this exemplary embodiment in an axial section as a kind of saw tooth profile. Correspondingly formed teeth of the second material of the connection piece 200 engage between the teeth 105*a*-105*n*.

The second material extends up to the edge 109 of the syringe body 2 such that the entire side wall 102 of the syringe main body 2 is formed of the cycloolefin.

The structure, both of the syringe main body 100 and of the connection piece 104/208, is in this exemplary embodiment formed as a regular structure, in which the distance from peak to peak or trough to trough is defined by the distance a between two peaks or two troughs. The mentioned peaks and troughs are also designated as protrusions or depressions.

The structure 104/208 also has a maximum depth t, which is defined by the vertical distance between the tip of a protrusion and the bottom of a depression.

The threaded connection 201 with the teeth 203 of the internal thread, which is opposite the nozzle 101, merges via a bead 205 in the region of the second material into the front wall 202 of the connection piece 200. This increases the mechanical strength in this region such that the risk of the threaded connection 201 breaking is reduced.

Inside the threaded connection 201, the base 207 of the threaded connection 203 reaches up to an inner corner 107, at which the front wall 103 of the syringe main body 100 merges into the nozzle 101. The nozzle 101 is therefore not covered by the second material. As a result, the material of the connection piece 200 does not come into contact with the medical fluid when used as intended.

Figure 7:
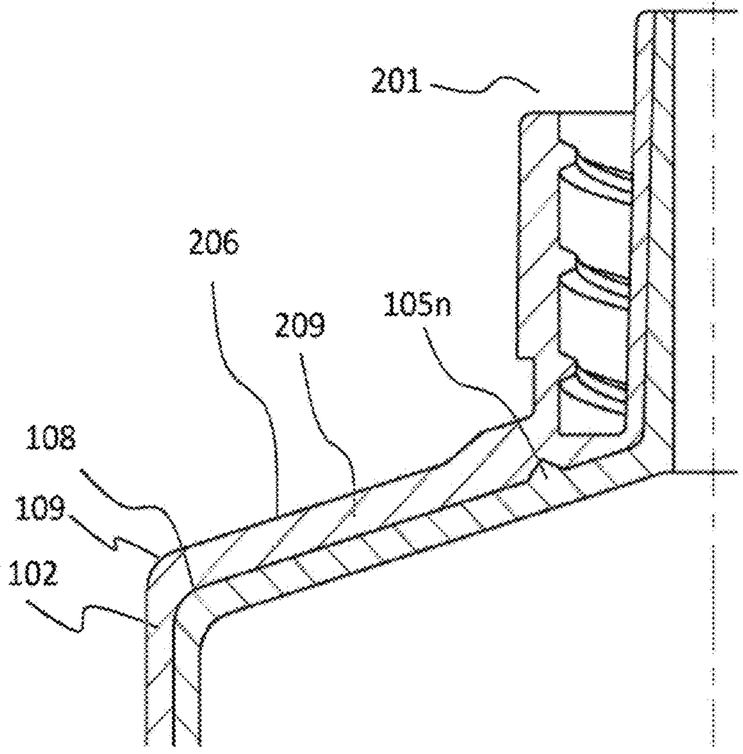
FIG. 7 is a sectioned view along the line C according to FIG. 5.

FIG. 7 is a sectioned view along the line C of FIG. 5. The section now runs through a radial groove 106 of the syringe main body 100. The groove 106 is formed by the teeth or rings 105*a*-105*m* of the structure 104 being interrupted in a radially extending strip. A corresponding web 209 of the second material has been formed in the groove 106. This web forms a torsion-proof connection in cooperation with the groove 106.

In this exemplary embodiment, a ring 105*n* reaching directly to the threaded connection 201 is not recessed by the groove 106. In the region of the web 209, this ring also forms a deflection point via which the introduction of stresses into the region of the web 209 is reduced.

The syringe main body 100 is also provided with a bead 108 at the edge. The upper side 206 of the connection piece 200 or of the front wall 4 of the syringe main body 2 aligns with the upper edge 109 of the side wall 102.

Figure 8:
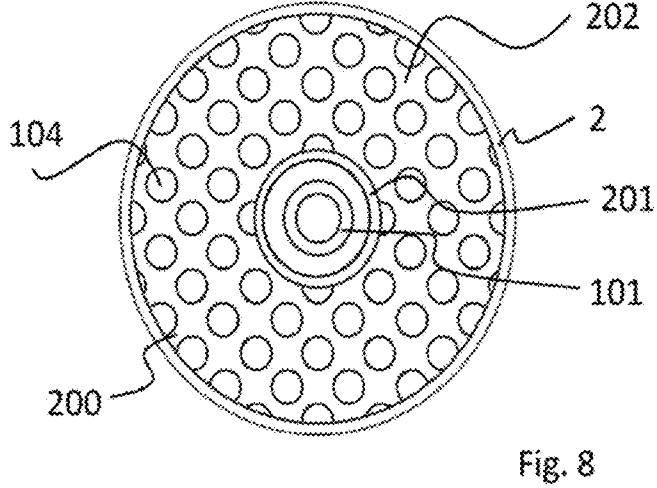
FIG. 8 and FIG. 9 are schematic views of alternative structures.
Figure 9:
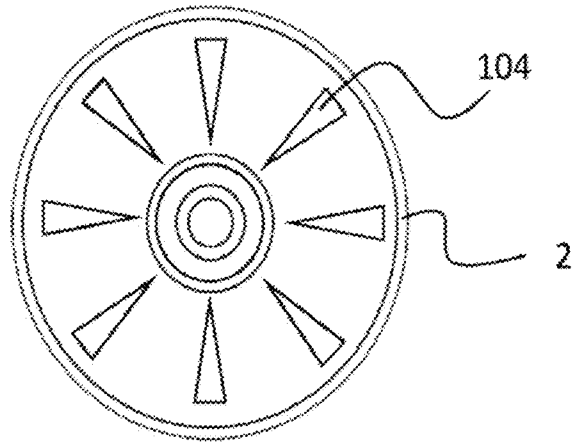

FIG. 8 and FIG. 9 show in a schematic top view of the front wall 4 of the syringe body 2 alternative embodiments of a structure.

According to the exemplary embodiment represented in FIG. 8, the syringe main body 100 comprises a structure 104, which is formed of a plurality of protruding nubs, which are distributed evenly in the two-layer region. This structure 104 is filled by the second material of the connection piece 200 and thus forms a form-fitting connection between the syringe main body 100 and the connection piece 200. A complementary configuration with indentations is also possible. The nubs would thereby be formed by the second material of the connection piece 200.

According to the exemplary embodiment represented in FIG. 9, the structure 104 comprises triangles, which are directed radially with the tip towards the middle point, as protrusions or depressions.

FIG. 10 is a flow diagram with the method steps according to an exemplary embodiment of the method according to the invention.

First, a syringe main body 100 with a nozzle 101 of a cycloolefin is injected. An injection-molding tool is used here which is formed in such manner that a front wall 103 of the syringe main body 100 comprises a structure 104.

Then, a connection piece 200 with a threaded connection 201 of a second material, in particular of a polypropylene, is molded onto the syringe main body 100.

The syringe body 2 now consisting of two different materials is characterized by a high strength of the connection, wherein the entire internal wall of the syringe main body 2 is formed of the cycloolefin.

LIST OF REFERENCE NUMERALS

1 Syringe
2 Syringe body
3 Inner volume
4 Front wall
100 Syringe main body
101 Nozzle
102 Side wall
103 Front wall
104 Structure of the syringe main body
105*a*-105*n* Ring/tooth
106 Radial groove
107 Corner
108 Bead
109 Edge
200 Connection piece
201 Threaded connection
202 Front wall
203 Tooth
205 Bead
206 Upper side
207 Base
208 Structure of the connection piece
209 Web

The invention claimed is:

1. A syringe body for a syringe, comprising:

a syringe main body having a longitudinal axis, a side wall, a front wall, and a nozzle arranged on the front wall, a front wall of the syringe body having a two-layer region with an internal wall and an external wall, the internal wall defined by the front wall of the syringe main body and having opposite distal front and proximal rear surfaces, the proximal rear surface of the internal wall and the side wall forming an internal volume, the external wall having opposite distal front and proximal rear surfaces, the distal front surface of the internal wall directly adjoining the proximal rear surface of the external wall to form a two-layer sandwich with the internal wall between the external wall and the internal volume, the syringe main body comprising, at least in portions, a cycloolefin as a first material, which first material forms the internal wall, and a connection piece with a threaded connection arranged on the external wall of the front wall of the syringe body, the connection piece, at least in portions, comprising a second plastic material different than the first material, wherein the syringe main body and the connection piece are integrally bonded to one another to form the syringe body, and wherein a structure extending distally from or proximally into the distal front surface of the internal wall and a complementary structure on the proximal rear surface of the external wall engage into one another with the structure between (i) the complementary structure and (ii) the internal volume in a direction along the longitudinal axis.

2. The syringe body according to claim 1, wherein the connection piece is provided as a separate part, which is mounted onto the syringe main body.

3. The syringe body according to claim 1, wherein the connection piece is molded onto the syringe main body.

4. The syringe body according to claim 1, wherein the distal front surface of the internal wall of the syringe body and the proximal rear surface of the external wall of the syringe body are integrally bonded to one another.

5. The syringe body according to claim 1, wherein the cycloolefin is at least one polymer selected from a group consisting of cycloolefin copolymer, cycloolefin polymer and crystal clear polymer.

6. The syringe body according to claim 5, wherein the structure extending distally from or proximally into the distal front surface of the internal wall of the syringe body is formed as a profile with a plurality of protrusions and/or depressions.

7. The syringe body according to claim 1, wherein the structure extending distally from or proximally into the distal front surface of the internal wall of the syringe body has at least one web and/or one groove, which extends from the nozzle at least in portions in the direction of the side wall.

8. The syringe body according to claim 1, wherein the structure extending distally from or proximally into the distal front surface of the internal wall of the syringe body is formed, at least in portions, in a fan-like and/or star-like manner.

9. The syringe body according to claim 1, wherein a layer of the second material is formed thickened around the threaded connection compared to a radially adjoining region of the layer of the second material.

10. The syringe body according to claim 1, wherein the structure extending distally from or proximally into the distal front surface of the internal wall of the syringe body is delimited by a radially circumferential web.

11. The syringe body according to claim 1, wherein the second material is softer than the first material.

12. The syringe body according to claim 1, wherein a ratio of structure depth to structure width is over 0.1.

13. The syringe body according to claim 12, wherein the ratio of structure depth to structure width is over 0.25.

14. The syringe body according to claim 12, wherein the ratio of structure depth to structure width is over 0.1 and under 1.

15. The syringe body according to claim 12, wherein the ratio of structure depth to structure width is over 0.1 and under 0.5.

16. The syringe body according to claim 1, wherein the ratio of structure depth to structure width is under 1.

17. The syringe body according to claim 16, wherein the ratio of structure depth to structure width is under 0.5.

18. The syringe body according to claim 1, wherein one of the structure and the complementary structure has a pattern of concentric ring-like protrusions combined with radial protrusions in a fan-like or star-like manner, and another of the structure and the complementary structure has a pattern of concentric ring-like depressions combined with radial depressions in the fan-like or star-like manner.

19. The syringe body according to claim 18, wherein the protrusions and depressions comprise at least one of a triangular cross-section, a wave cross-section, and a sinusoidal cross-section.

20. A method for manufacturing a syringe body for a syringe according to claim 1, comprising the steps:

injecting the syringe main body of the cycloolefin as the first material, wherein the structure has depressions extending proximally into the distal front surface of the internal wall of the syringe main body, molding the connection piece having the threaded connection of the second material onto the distal front surface of the internal wall, wherein the depressions of the structure are filled with the second material such that the structure on the distal front surface of the internal wall of the syringe body and the complementary structure on the proximal rear surface of the external wall engage into one another.

* * * * *